US012751860B2

(12) United States Patent
Sheridan et al.

(10) Patent No.: US 12,751,860 B2
(45) Date of Patent: Oct. 6, 2026

(54) EYE DROPPER TARGETING DEVICE AND METHOD

(71) Applicant: VERILY LIFE SCIENCES LLC, Dallas, TX (US)

(72) Inventors: Martin Sheridan, El Granada, CA (US); Tim Stowe, Alameda, CA (US); Dimitri Azar, Chicago, IL (US)

(73) Assignee: Verily Health Inc., Dallas, TX (US)

( * ) Notice: Subject to any disclaimer, the term of this patent is extended or adjusted under 35 U.S.C. 154(b) by 351 days.

(21) Appl. No.: 18/227,879

(22) Filed: Jul. 28, 2023

(65) Prior Publication Data

US 2024/0033126 A1 Feb. 1, 2024

Related U.S. Application Data

(60) Provisional application No. 63/393,002, filed on Jul. 28, 2022.

(51) Int. Cl.
*A61F 9/00* (2006.01)

(52) U.S. Cl.
CPC .................................. *A61F 9/0026* (2013.01)

(58) Field of Classification Search
CPC . A61F 9/0026; A61F 9/0008; G01C 9/00–36; A61M 2205/583; A61M 2205/585
See application file for complete search history.

(56) References Cited

U.S. PATENT DOCUMENTS 771,803 A * 10/1904 Bishop

FOREIGN PATENT DOCUMENTS

| | | | |
|---|---|---|---|
| CN | 102805708 A | * | 12/2012 |
| CN | 206342598 U | * | 7/2017 |
| JP | S5880246 U | * | 5/1983 |
| JP | 2007037775 A | * | 2/2007 |
| JP | 6997368 B1 | * | 1/2022 |

(Continued)

OTHER PUBLICATIONS

International Searching Authority, International Search Report and Written Opinion of the International Searching Authority, International Application No. PCT/US2023/029045, 12 pages, ISA/EPO.

*Primary Examiner* — Leslie R Deak
*Assistant Examiner* — Linnae E. Raymond
(74) *Attorney, Agent, or Firm* — Christensen O'Connor Johnson Kindness PLLC

(57) ABSTRACT

An apparatus for assisting with alignment of a dropping nozzle of an eye dropper bottle includes a tubular hub configured for selective engagement with the dropping nozzle to laterally surround the dropping nozzle within a hub lumen thereof. A first semispherical disc has a first center aperture which laterally surrounds an outer wall of the tubular hub and a first disc body which is semispherically curved. A second semispherical disc has a second center aperture which laterally surrounds the outer wall of the tubular hub and a second disc body which is semispherically curved. The first and second disc rims are attached together at a rim perimeter to laterally enclose a substantially fluid tight toroidal indicator space. At least one user-perceptible liquid is located within the indicator space, the liquid shifting with respect to the tubular hub under influence of gravity responsive to an angular position of the tubular hub.

18 Claims, 9 Drawing Sheets

(56) References Cited

FOREIGN PATENT DOCUMENTS

| | | | | |
|---|---|---|---|---|
| WO | 9712579 | A1 | 4/1997 | |
| WO | WO-2004044524 | A2 * | 5/2004 | ............... G01C 9/26 |
| WO | WO-2012072546 | A1 * | 6/2012 | ........... A61F 9/0026 |

* cited by examiner

EYE DROPPER TARGETING DEVICE AND METHOD

RELATED APPLICATION

This application claims priority from U.S. Provisional Application No. 63/393,002, filed 28 Jul. 2022, the subject matter of which is incorporated herein by reference in its entirety.

TECHNICAL FIELD

This disclosure relates to an apparatus and method for assisting with alignment of a dropping nozzle of an eye dropper bottle and, more particularly, to a method and apparatus for aligning a dropping nozzle of an eye dropper bottle with an eye of a patient.

BACKGROUND

It can be difficult for a patient to align an eye dropper bottle with her eyeball sufficiently to target the gravity-driven insertion of an eyedrop liquid precisely into the eye. Repeated unsuccessful attempts to self-administer the eye-drops can result in mess and wasted liquid, as well as patient discomfort and anxiety. As a result, it may be desirable in some use environments to provide the patient with some indication of the position of the eye dropper in relation to the eyeball, before the bottle is squeezed to release a drop of the liquid.

SUMMARY

In an aspect, alone or in combination with any other aspect, an apparatus for assisting with alignment of a dropping nozzle of an eye dropper bottle is described. A tubular hub is configured for selective engagement with the dropping nozzle to selectively laterally surround the dropping nozzle within a hub lumen thereof. A first semispherical disc has a first center aperture and a first disc rim, spaced radially apart from the first center aperture by a first disc body. The first center aperture laterally surrounds an outer wall of the tubular hub. The first disc body is semispherically curved between the first center aperture and the first disc rim. A second semispherical disc has a second center aperture and a second disc rim, spaced radially apart from the second center aperture by a second disc body. The second center aperture laterally surrounds the outer wall of the tubular hub at a location thereupon longitudinally spaced from the first center aperture. The second disc body is semispherically curved between the second center aperture and the second disc rim. The first and second disc rims are attached together at a rim perimeter to laterally enclose a substantially fluid tight toroidal indicator space longitudinally between the first and second disc bodies and radially between the outer wall of the tubular hub and the rim perimeter. At least one user-perceptible liquid is located within the indicator space. The liquid shifts with respect to the tubular hub under influence of gravity responsive to an angular position of the tubular hub.

In an aspect, alone or in combination with any other aspect, a method of aligning a dropping nozzle of an eye dropper bottle with an eye of a patient is described. An apparatus is provided, including a tubular hub, a first semispherical disc having a first center aperture and a first disc rim, spaced radially apart from the first center aperture by a first disc body. The first center aperture laterally surrounds an outer wall of the tubular hub, and the first disc body is semispherically curved between the first center aperture and the first disc rim. A second semispherical disc has a second center aperture and a second disc rim, spaced radially apart from the second center aperture by a second disc body. The second center aperture laterally surrounds the outer wall of the tubular hub at a location thereupon longitudinally spaced from the first center aperture. The second disc body is semispherically curved between the second center aperture and the second disc rim. The first and second disc rims are attached together at a rim perimeter to laterally enclose a substantially fluid tight toroidal indicator space longitudinally between the first and second disc bodies and radially between the outer wall of the tubular hub and the rim perimeter. At least one user-perceptible liquid is located within the indicator space. A position of the user-perceptible liquid within the indicator space is shifted with respect to the tubular hub under influence of gravity responsive to an angular position of the tubular hub. The dropping nozzle is engaged with the tubular hub to selectively laterally surround the dropping nozzle within a hub lumen. The liquid is substantially symmetrically distributed within the indicator space, surrounding the tubular hub, to indicate that the dropping nozzle is substantially vertically located with respect to a ground surface.

BRIEF DESCRIPTION OF THE DRAWINGS

For a better understanding, reference may be made to the accompanying drawings, in which.

DESCRIPTION OF ASPECTS OF THE DISCLOSURE

Unless defined otherwise, all technical and scientific terms used herein have the same meaning as is commonly understood by one of skill in the art to which the present disclosure pertains.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

Figure 1:
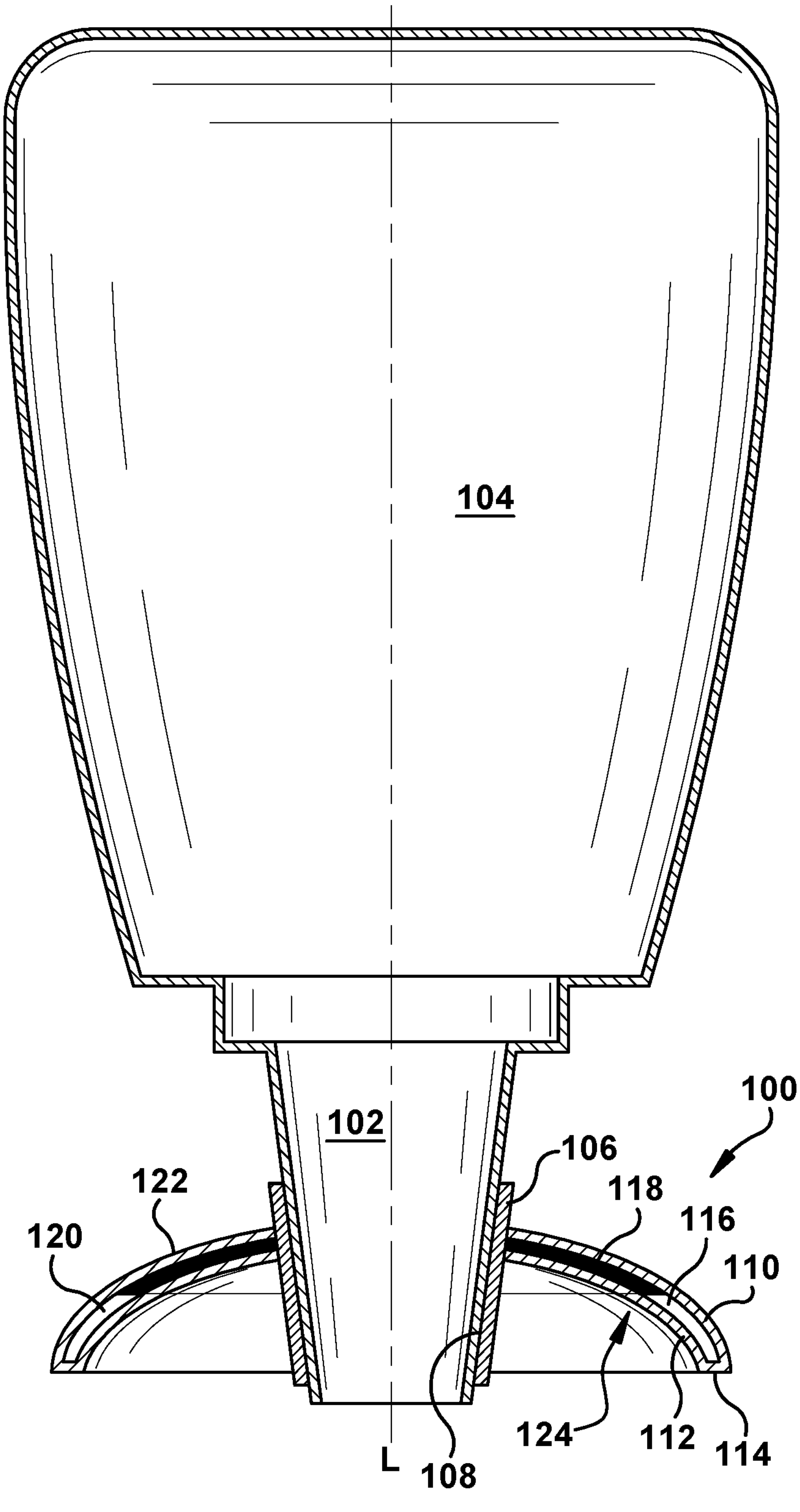
FIG. 1 is a schematic cross sectional view of an apparatus according to a first embodiment, as used with an eye dropper bottle.
Figure 2:
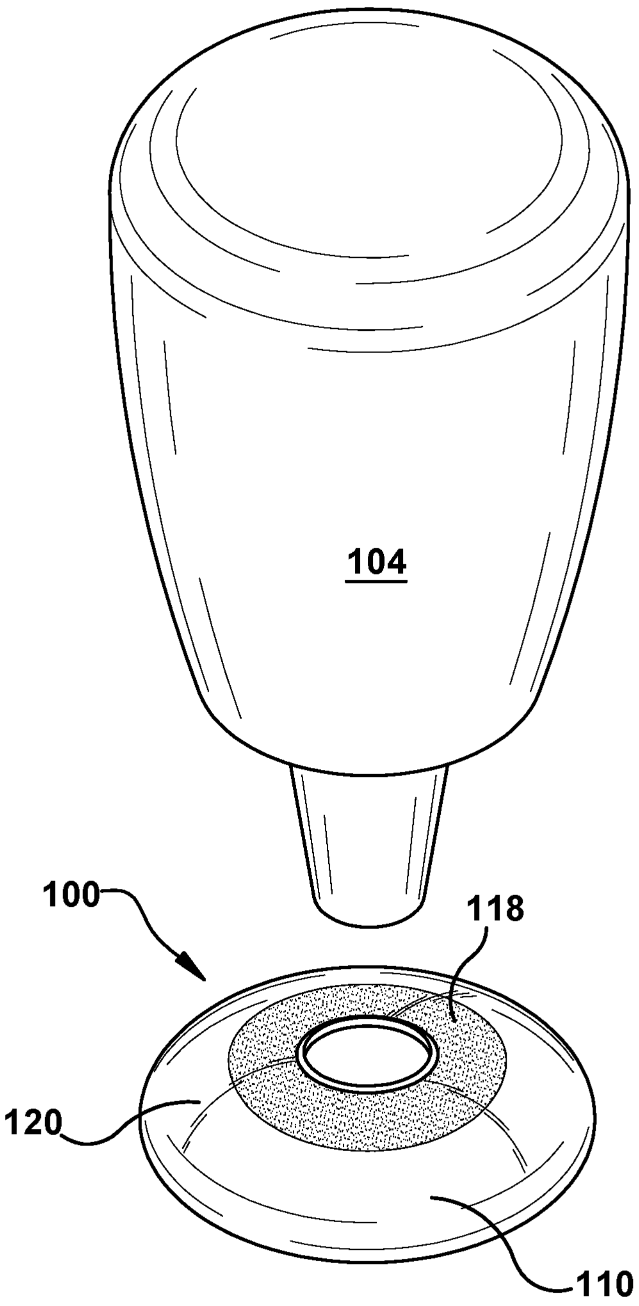
FIG. 2 is a schematic partial perspective view of the apparatus of FIG. 1 and the eye dropper bottle.

FIGS. 1-3 schematically depict an apparatus 100 for assisting with alignment of a dropping nozzle 102 of an eye dropper bottle 104 in a first embodiment. The apparatus 100 includes a tubular hub 106 configured for slidable engagement with the dropping nozzle 102 to selectively laterally surround the dropping nozzle 102 within a hub lumen 108 of the tubular hub 106. The term "lateral", as used herein, references a direction substantially perpendicular to a longitudinal direction (e.g., central axis L, in the Figures), which is substantially vertical in the orientation of FIG. 1. For clarity of depiction, a tubular hub is intentionally omitted from many of the Figures; however, one of ordinary skill in the art will readily be able to provide a suitable tubular hub for an apparatus 100 in a particular use environment of the present invention.

The tubular hub 106 may be a truncated cone with the hub lumen 108 configured to accept a conical dropping nozzle 102 in a slidable, friction-fit type manner. Alternatively, the hub lumen could be configured to threadedly, ratchet-type, or otherwise selectively accept a dropping nozzle 102 having a crenellated or other non-smooth profile, which may be helpful in maintaining the apparatus 100 on the dropping nozzle 102.

Figure 18:
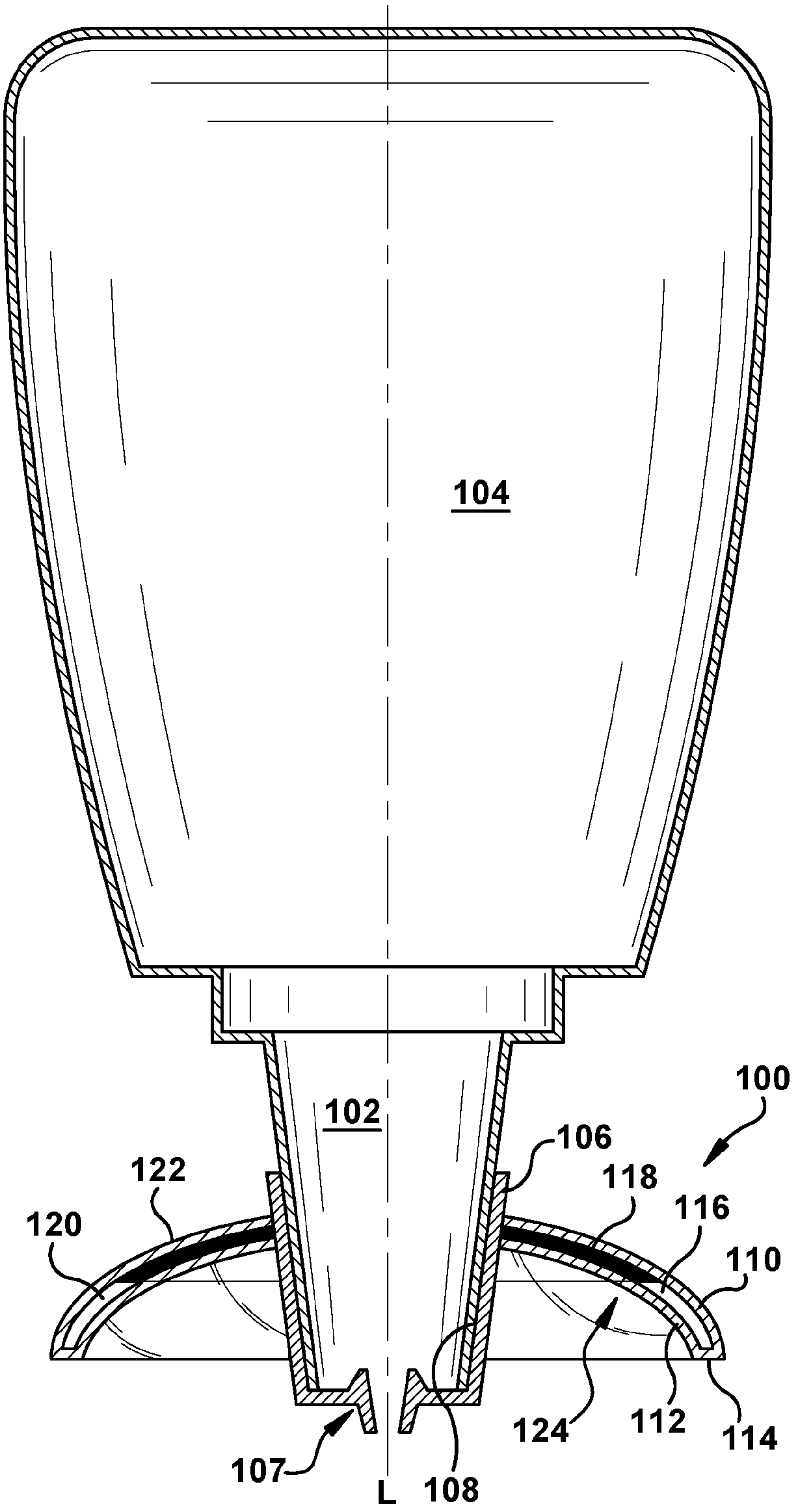
FIG. 18 is a schematic cross sectional view of the apparatus of FIG. 1 including an example alternative configuration of a component.

It is contemplated that the tubular hub 106 could comprise at least a portion of the dropping nozzle 102 itself, and/or be formed integrally therewith. Alternatively, the tubular hub 106 could be separate from the dropping nozzle 102 and thus may be configured for selective engagement with the eye dropper bottle 104. FIG. 18 schematically depicts an example alternative configuration for the tubular hub 106 which provides a predetermined amount of flow restriction to the dropping nozzle 102 for any desired reason such as, but not limited to, reducing "waste" of excess medicine running out of the eye, and/or have a prescription to "micro-dose"—i.e., use a smaller drop size which may be, for example, in the 10-20 microliter range. This flow restriction is at least partially provided via tip obstructor 107 which occludes at least a portion of the available cross-sectional flow area of the dropping nozzle 102 to restrict the amount of fluid flow permitted to egress the eye dropper bottle 104. The tip obstructor 107 could be integrally formed with the tubular hub 106, manufactured separately therefrom for later attachment, or provided in any other suitable manner. The tip obstructor 107 may have any desired configuration (e.g. can include the pictured "guide collar" surrounding the fluid hole to assist with dispensing) and may be provided by one of ordinary skill in the art for a particular use environment of the apparatus 100.

With reference back now to FIGS. 1-3, a first semispherical disc 110 has a first center aperture and a first disc rim, spaced radially apart from the first center aperture by a first disc body. The "radial" direction, as used herein, represents a direction toward and away from a central longitudinal axis "L" of the apparatus. The first center aperture laterally surrounds an outer wall of the tubular hub 106. The first disc body is semispherically curved between the first center aperture and the first disc rim.

A second semispherical disc 112 has a second center aperture and a second disc rim, spaced radially apart from the second center aperture by a second disc body. The second center aperture laterally surrounds the outer wall of the tubular hub 106 at a location thereupon longitudinally spaced from the first center aperture, and the second disc body is semispherically curved between the second center aperture and the second disc rim.

The first and second disc rims are attached together at a rim perimeter 114 to laterally enclose a substantially fluid tight toroidal indicator space 116 longitudinally between the first and second disc bodies and radially between the outer wall of the tubular hub 106 and the rim perimeter 114. The first and second disc rims could be attached directly together at the rim perimeter 114, though it is also contemplated that an intermediate or bridging member could span a longitudinal space between the first and second disc rims to attach them indirectly together at the rim perimeter 114. One or both of the first and second discs 110, 112 could be integrally formed with at least a portion of the tubular hub 106.

At least one user-perceptible liquid 118 is located within the indicator space 116. The liquid 118 shifts with respect to the tubular hub 106 under influence of gravity responsive to an angular position of the tubular hub 106. Accordingly, the apparatus 100 is configured to function in a "bullseye level" or "spirit level" manner, in which a position of the user-perceptible liquid 118 within the indicator space 116 functions to indicate an orientation of the apparatus 100, and thus of the eye dropper bottle 104 to which it is (at least temporarily) engaged.

A first, substantially transparent liquid 120 and a second, user-perceptible liquid 118 may be concurrently located within the indicator space 116. In such situations, it is contemplated that the second liquid 118 may be urged toward the tubular hub 106 responsive to the relative densities of the first and second liquids 120 and 118, via gravitational influence. It is contemplated that the two fluids 118 and 120 should be immiscible and of different densities, so as to separate into two unique liquid domains under the influence of gravity. For example, in certain use environments, the first liquid 120 may be water (having a density of about 1 g/cc) and the second liquid 118 may be mineral oil (with a density in the range of about g/cc), or vice versa. As another example, the two liquids need not be water and oil but could be two different types of immiscible oils such as the aforementioned mineral oil and silicone oil (with a density in the range of 0.95-0.97 g/cc) that also will not chemically mix due to a predetermined selection of molecular weights. At least one of the first and second liquids may be dyed to assist with user-perceptibility thereof. It is also contemplated that at least a portion of the indicator space could be "head space" and occupied by air or another gas, instead of another liquid. One of ordinary skill in the art will be readily able to provide a suitable liquid and/or combination of fluid(s) for a particular use environment.

The user-perceptible liquid 118 may be substantially symmetrically distributed within the indicator space 116, surrounding the tubular hub 106, when the tubular hub 106 is substantially vertically located with respect to a ground surface. This is the situation shown in at least FIGS. 3 and 4A-4B.

A chosen one of the first and second discs 110 and 112 may include a diffuser coating 122 on at least a portion of the disc body. The diffuser coating 122, when present, may be a different color from a color of the user-perceptible liquid 118 and/or could be at least partially translucent. For example, in the apparatus 100 of the first embodiment, a diffuser coating 122 may be located on the topmost surface of the top (here, first) disc 110. The diffuser coating 122, when present, may assist the user with perceiving the user-perceptible liquid 118, such as by providing contrast against a background color/view. (It is contemplated that the diffuser coating 122 may be located at least partially within the indicator space 116, to avoid chipping or wearing away of the coating.)

A chosen one of the first and second discs 110 and 112 may include a reflective coating 124 on at least a portion of the disc body. The term "reflective coating" is used herein to indicate a substance or surface treatment, located on part or all of another structure, which is configured to at least partially reflect (back toward the originating direction) at least a portion of the light rays incident upon the reflective coating. Examples of reflective coatings include, but are not limited to, a reflective optically smooth mirror coating, a highly polished substrate surface, a half-silvered coating which allows partial transmission of incident light, a thin reflective sheet which can be adhered to a substrate, or any other suitable thin-layer optically active substance. (It is contemplated that the reflective coating 124 may be located at least partially within the indicator space 116, to avoid chipping or wearing away of the coating.) When present, the reflective coating 124 may face longitudinally downward to selectively reflect at least a portion of a user's eye, when the tubular hub 106 is engaged with the dropping nozzle 102. The reflective coating 124 may be at least partially translucent, or include discontinuities or "breaks" in the pattern of coverage, whether or not the reflective coating 124 is at least partially translucent.

When present, and when located in a position longitudinally interposed between the user-perceptible liquid 118 and the user's eye, the reflective coating 124 may be configured to allow viewing of the user-perceptible liquid 118 therethrough (via transmission of light longitudinally through the reflective coating 124) in addition to and concurrently with reflecting at least a portion of the incident light (image) back toward the user's eye. Alternatively, when the reflective coating 124 is located in a position "behind" the user-perceptible liquid 118 and the user's eye, the reflective coating 124 may be configured to reflect back substantially all of the incident light, with no meaningful transmission of light through the reflective coating 124.

As a result of the reflective coating 124, the user may be able to view a reflected image of at least a portion of her eye (e.g., the iris and/or pupil) and thus be able to align the dropper bottle 104 not only vertically (through the "bullseye level" effect of the user-perceptible liquid 118) but in a predetermined position with respect to the eyeball (e.g., directly above the pupil). The chosen first or second disc 110 or 112 which includes the reflective coating 124 could be convexly or concavely shaped, with a desired radius of curvature, to achieve a predetermined optical reflective effect, as perceived by the user. The shape and radius of curvature of the semi-hemisphere onto which the coating 124 is placed may be selected to present to the user a magnified image of their own eye to visually depict a mirrored image showing alignment of the dropper bottle 104. This radius of curvature may be predetermined at an appropriate value for some users who have difficulty putting drops in their eyes due to presbyopia, to compensate for a potentially lowered ability of that user to focus and accommodate their focus to nearby objects. Thus, the chosen first or second disc 110 or 112 can correct for the lack of good native patient focus, in some use environments, in addition to adding magnification power. One of ordinary skill in the art will be readily able to provide suitably configured first and second discs 110 and 112, with any desired coatings, to achieve desired results (e.g., predetermined vertical distance of the apparatus 100 from the eyeball) for a particular use environment of the apparatus 100.

At least one of the first and second discs 110 and 112 may be concave in a top-to-bottom direction of the apparatus 100, such that the corresponding disc rim is located below the disc center aperture. This is the arrangement shown in the apparatus 100 of FIGS. 1-5B, according to a first embodiment, and in the apparatus 100 of FIGS. 5-7, according to the second embodiment.

Figure 3A:
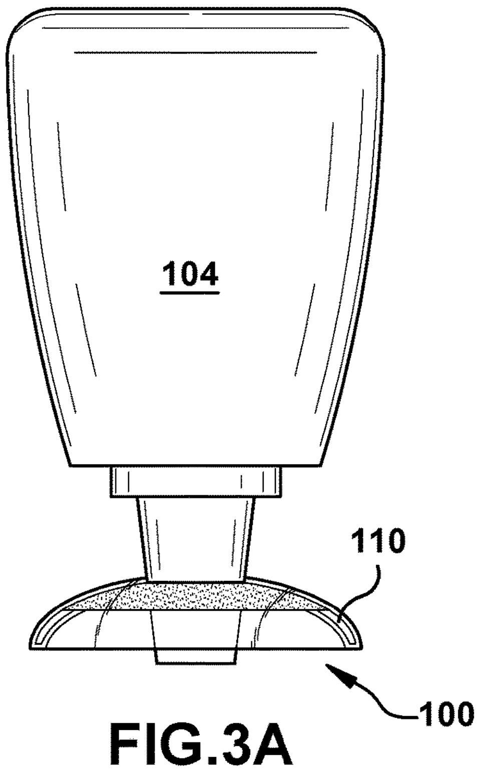
FIG. 3A is a schematic partial side view of the apparatus of FIG. 1 engaged with the eye dropper bottle in a first, vertical position.
Figure 4A:
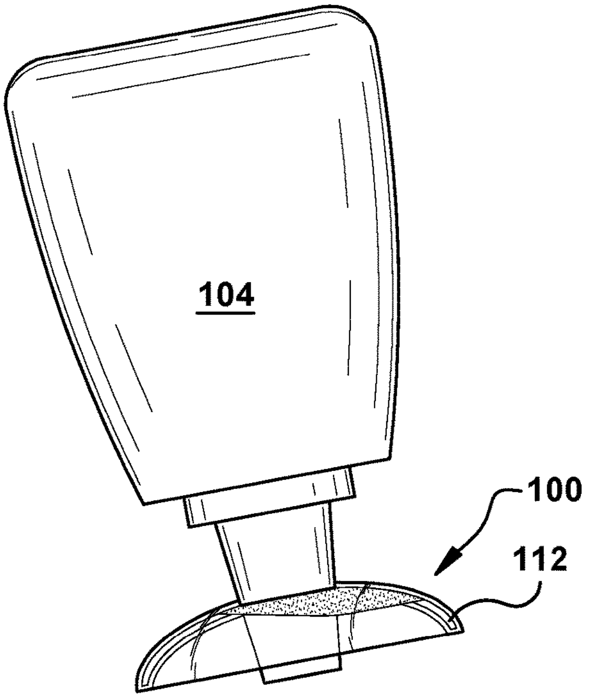
FIG. 4A is a schematic partial side view of the apparatus of FIG. 1 engaged with the eye dropper bottle in a second, non-vertical position.
Figure 3B:
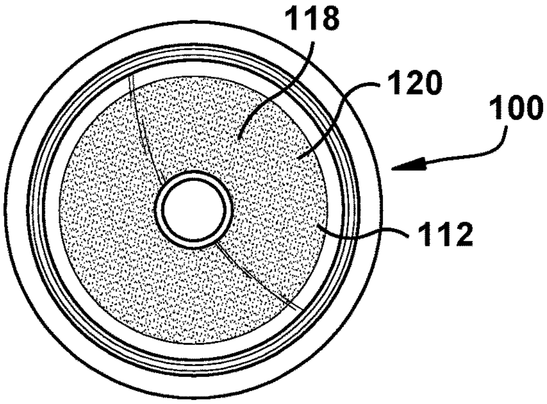
FIG. 3B is a schematic bottom view of the apparatus of FIG. 1 in the first, vertical position.
Figure 4B:
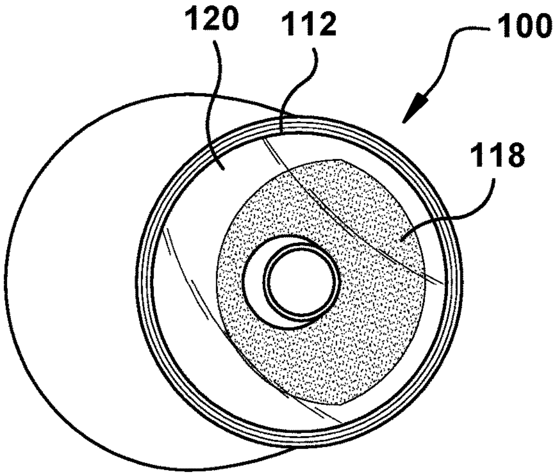
FIG. 4B is a schematic bottom view of the apparatus of FIG. 1 in the second, non-vertical position.

FIGS. 3A-4B schematically depict the way in which a position of the user-perceptible liquid 118 can shift within the indicator space 116 with respect to the tubular hub 106 under influence of gravity responsive to an angular position of the tubular hub 106, in a bubble level (A.K.A., bullseye level, sphere level, spirit level, etc.) manner, to help indicate verticality of the apparatus 100 and thus the attached dropper bottle 104. The user can tilt, precess, or otherwise move the dropper bottle until the user-perceptible liquid 118 is substantially symmetrically distributed within the indicator space, surrounding the tubular hub, as shown in FIGS. 3A-3B, to indicate that the dropping nozzle 102 is substantially vertically located with respect to a ground surface. When the reflective coating 124 is present, the apparatus 100 can indicate to the user, via concurrent viewing of the user-perceptible liquid 118 and the reflected image of at least the portion of the user's eye, that a predetermined alignment position of the dropper nozzle 104 with the user's eye has been achieved. The user may then squeeze or otherwise manipulate the bottle to dispense a drop of the medicament or other dropped liquid, with confidence that the dropper bottle 104 is in an appropriate dispensing position to achieve a successful application to the eye.

Figure 5:
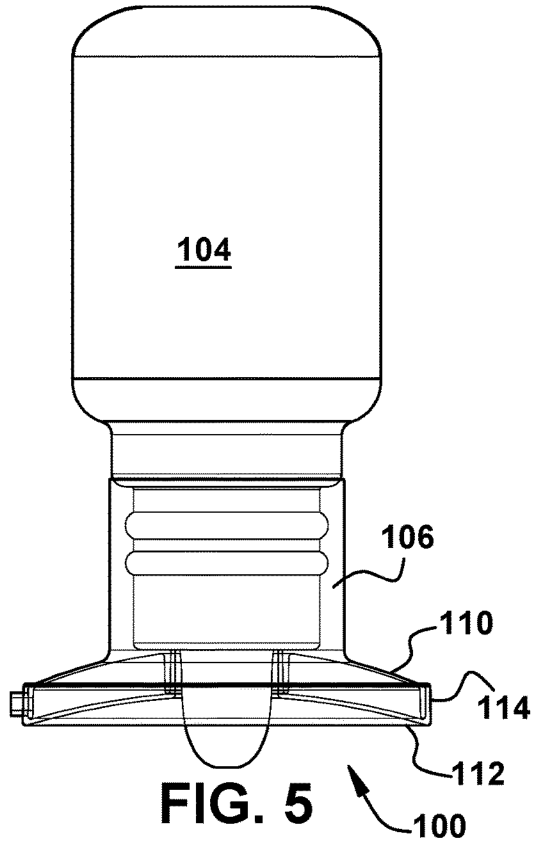
FIG. 5 is a schematic side view of an apparatus according to a second embodiment, as used with an eye dropper bottle.
Figure 6:
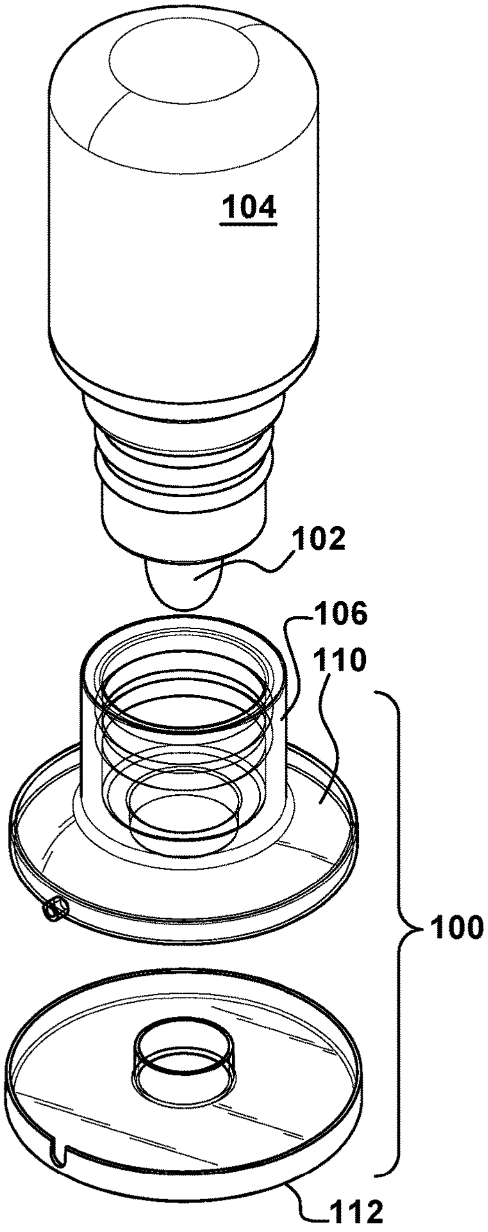
FIG. 6 is an exploded schematic side perspective view of the apparatus of FIG. 5.
Figure 7:
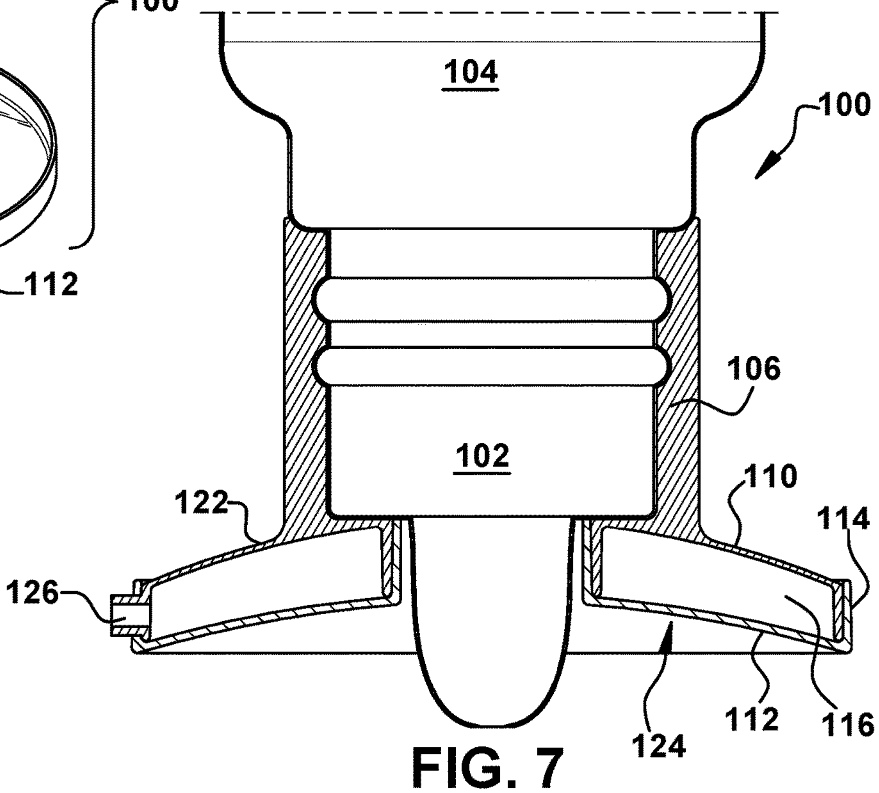
FIG. 7 is a schematic cross sectional view of the apparatus of FIG. 5.
Figure 8:
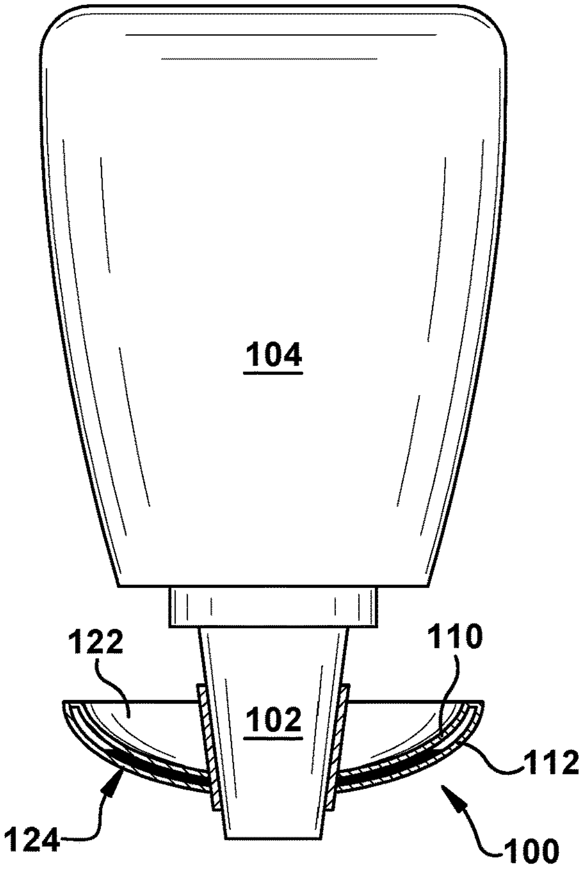
FIG. 8 is a schematic cross sectional view of an apparatus according to a third embodiment, as used with an eye dropper bottle.
Figure 9:
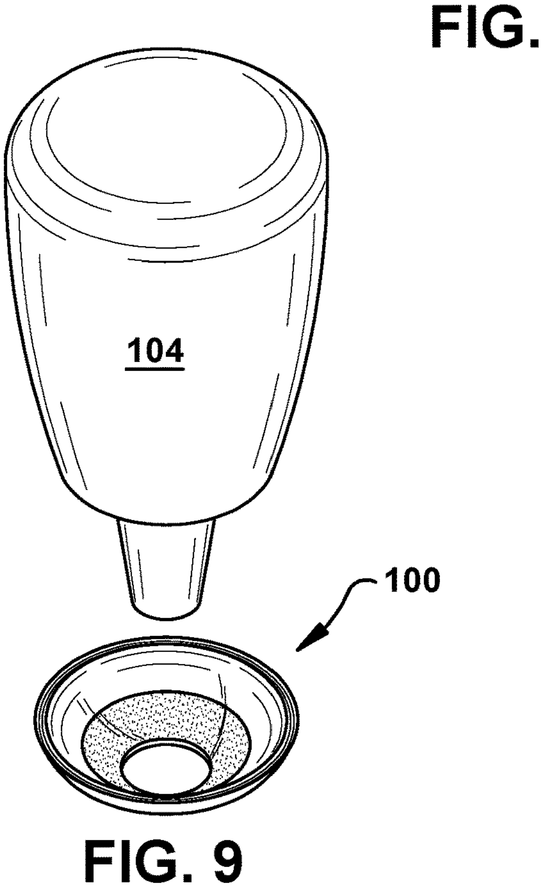
FIG. 9 is a schematic partial perspective view of the apparatus of FIG. 8 separated from the eye dropper bottle.
Figure 10:
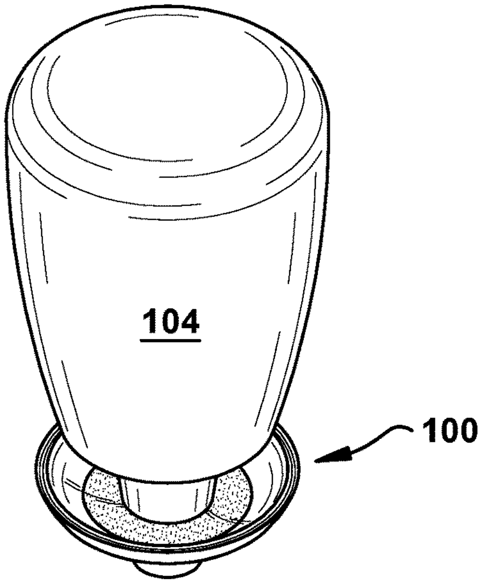
FIG. 10 is a schematic partial perspective view of the apparatus of FIG. 8 engaged with the eye dropper bottle.
Figure 11A:
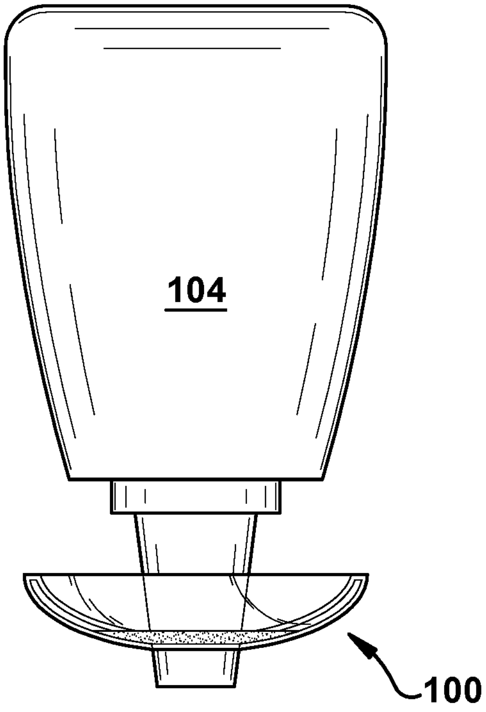
FIG. 11A is a schematic partial side view of the apparatus of FIG. 8 engaged with the eye dropper bottle in a first, vertical position.
Figure 12A:
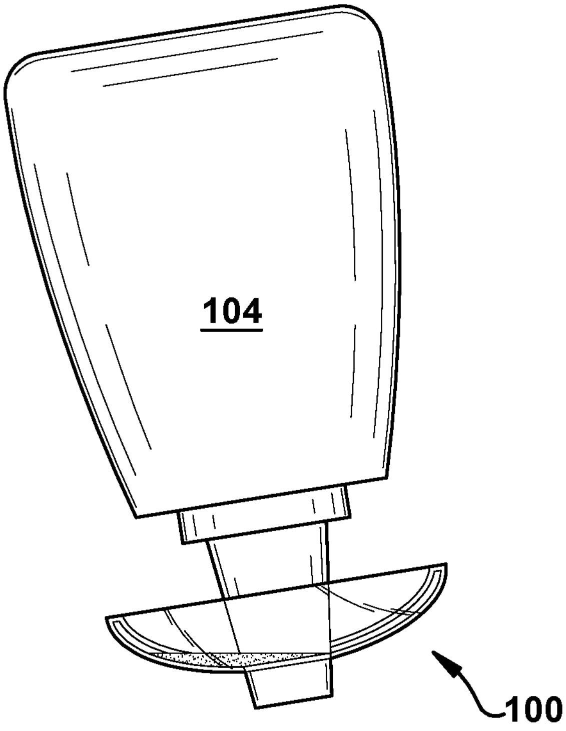
FIG. 12A is a schematic partial side view of the apparatus of FIG. 8 engaged with the eye dropper bottle in a second, non-vertical position.
Figure 11B:
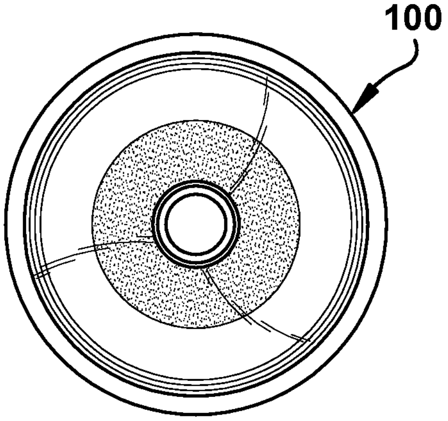
FIG. 11B is a schematic bottom view of the apparatus of FIG. 8 in the first, vertical position.
Figure 12B:
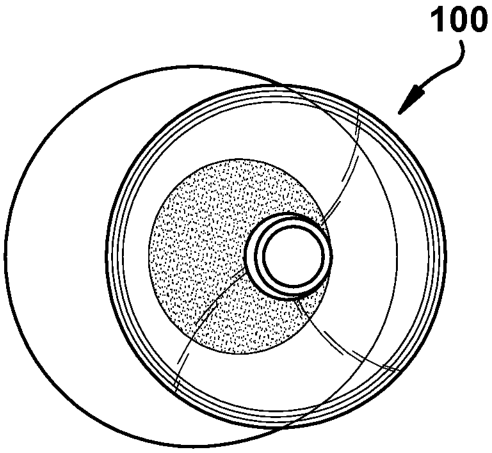
FIG. 12B is a schematic bottom view of the apparatus of FIG. 8 in the second, non-vertical position.

FIGS. 5-7 illustrate a second embodiment of an apparatus 100. The apparatus 100 of FIGS. 5-7 is similar to the previously described apparatus. Description of common elements and operation similar to those in the previously described first embodiment will not be repeated with respect to the second embodiment, but should instead be considered to be incorporated by reference as appropriate.

In the apparatus 100 of FIGS. 5-7, the first disc 110 is integrated into a structure which also comprises at least a portion of the tubular hub 106. The hub lumen 108 is shaped for at least one of a screwed or ribbed/gripping style connection with the dropping nozzle 102. One of ordinary skill in the art can readily provide a suitably configured tubular hub 106 (and/or other structure(s) of the apparatus 100) for use with a particular type of dropper bottle 104.

A fill port 126 is provided to assist with placement of the at least one user-perceptible liquid 118—and/or any other fluid—within the indicator space 116. After filling of the indicator space 116 as desired, the fill port 126 may be welded, fused, plugged, melted, or otherwise closed in a substantially fluid tight manner. FIG. 5 also schematically depicts the structure of certain commercially available preservative free bottles. Dropper bottles 104 such as those shown in FIG. 5 typically have a threaded or push on section for a cap that is much taller than those used with other commercially available bottles. One of ordinary skill in the art can configure an apparatus 100 which attaches to a dropper bottle 104, such as that shown in FIG. 5, via engagement with the threaded or push on section as noted.

FIGS. 8-12B illustrate a third embodiment of an apparatus 100. The apparatus 100 of FIGS. 8-12B is similar to the previously described apparatuses. Description of common elements and operation similar to those in the previously described embodiments will not be repeated with respect to the third embodiment, but should instead be considered to be incorporated by reference as appropriate.

As shown in the apparatus 100 of FIGS. 8-12B, at least one of the first and second discs 110 and 112 may be convex in a top-to-bottom direction of the apparatus 100, such that the corresponding disc rim is located above the disc center aperture. This is the arrangement shown in the apparatus 100 of FIGS. 8-12B, according to the third embodiment, in the apparatus 100 of FIG. 13, according to a fourth embodiment, and in the apparatus 100 of FIGS. 14-17B, according to a fifth embodiment. When at least one of the first and second discs 110 and 112 is convex in this manner, gravity can work upon the user-perceptible fluid 116, and the second, higher-density fluid is not needed to effectuate the "bullseye level" effect as depicted in the Figures.

Figure 13:
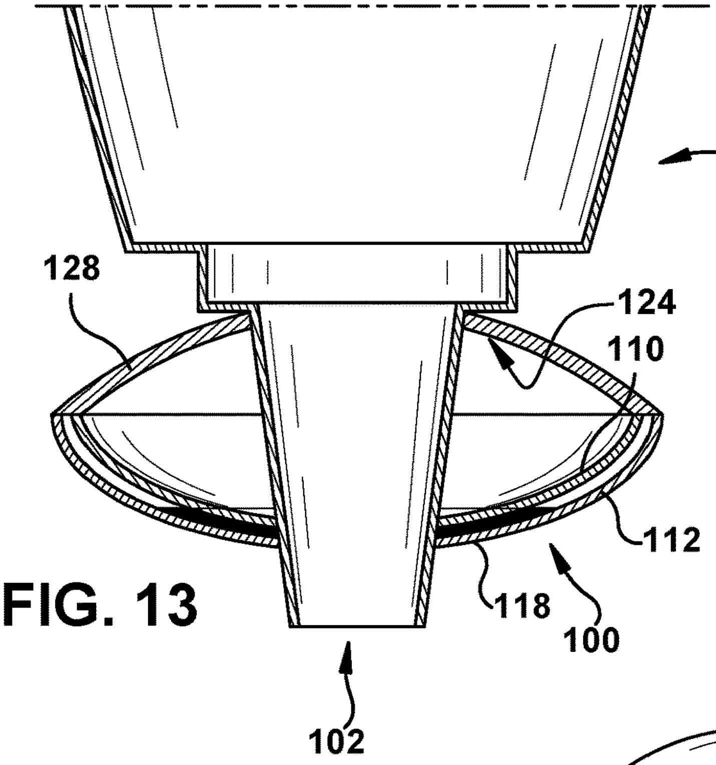
FIG. 13 is a partial schematic cross-sectional view of an apparatus according to a fourth embodiment, as used with an eye dropper bottle.

FIG. 13 illustrates a fourth embodiment of an apparatus 100. The apparatus 100 of FIG. 13 is similar to the previously described apparatuses. Description of common elements and operation similar to those in the previously described embodiments will not be repeated with respect to the fourth embodiment, but should instead be considered to be incorporated by reference as appropriate.

The apparatus 100 of FIG. 13 includes an auxiliary disc 128 which is located longitudinally spaced from both the first and second discs 110 and 112. The auxiliary disc 128 has an opposite curvature (here, concave) to the (here, convex) curvature of the first and second discs 110 and 112. The auxiliary disc 128 includes a reflective coating 124, which can be opaque due to its "backing position" on the apparatus 100, with the user-perceptible liquid 118 interposed longitudinally between the user's eye and the reflective coating 124 during administration of the eye drops. It is contemplated, though, that the user-perceptible liquid 118 may be desirably translucent to allow viewing of the reflected eye image in the apparatus 100 as shown in FIG. 13, however.

FIGS. 14-17B illustrate a fifth embodiment of an apparatus 100. The apparatus 100 of FIGS. 14-17B is similar to the previously described apparatuses. Description of common elements and operation similar to those in the previously described embodiments will not be repeated with respect to the fifth embodiment, but should instead be considered to be incorporated by reference as appropriate.

Here, as with the apparatus 100 of the fourth embodiment, the apparatus 100 shown in FIGS. 14-17B includes an auxiliary disc 128, which is oppositely curved as compared to the first and second discs 110 and 112. However, the auxiliary disc 128 of the fifth embodiment is located "below" the indicator space 116, interposed longitudinally between the user's eye and the first and second discs 110 and 112. As a result, the reflective coating 124 on the auxiliary disc 128 in FIGS. 14-17B should be translucent, patterned, or otherwise configured for the user to view the user-perceptible liquid therethrough.

Figure 14:
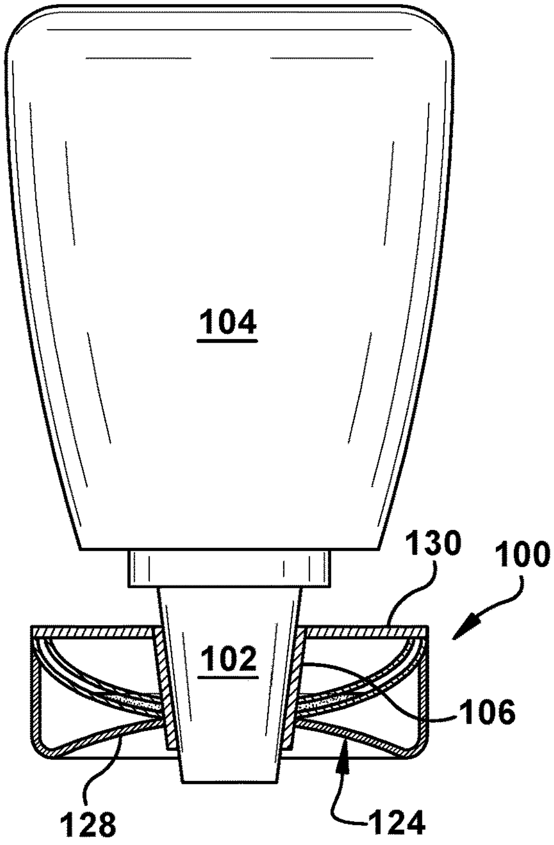
FIG. 14 is a schematic cross sectional view of an apparatus according to a fifth embodiment, as used with an eye dropper bottle.
Figure 15:
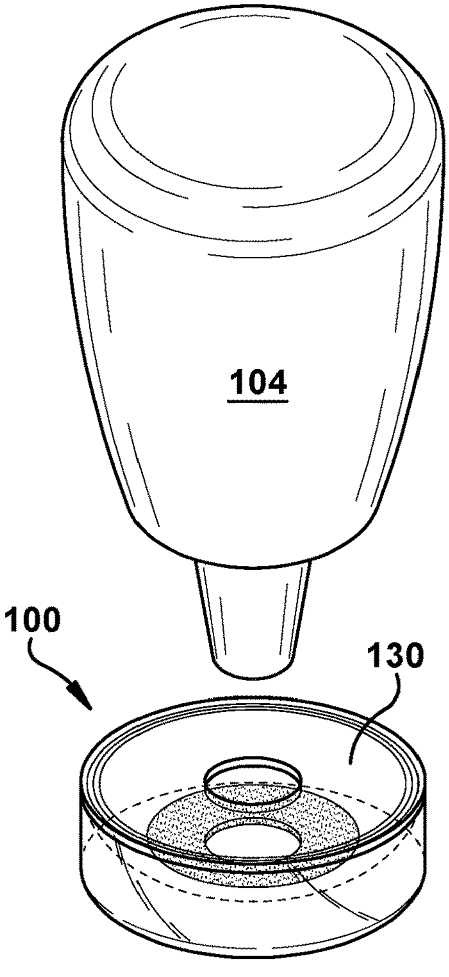
FIG. 15 is a schematic partial perspective view of the apparatus of FIG. 14 separated from the eye dropper bottle.
Figure 16A:
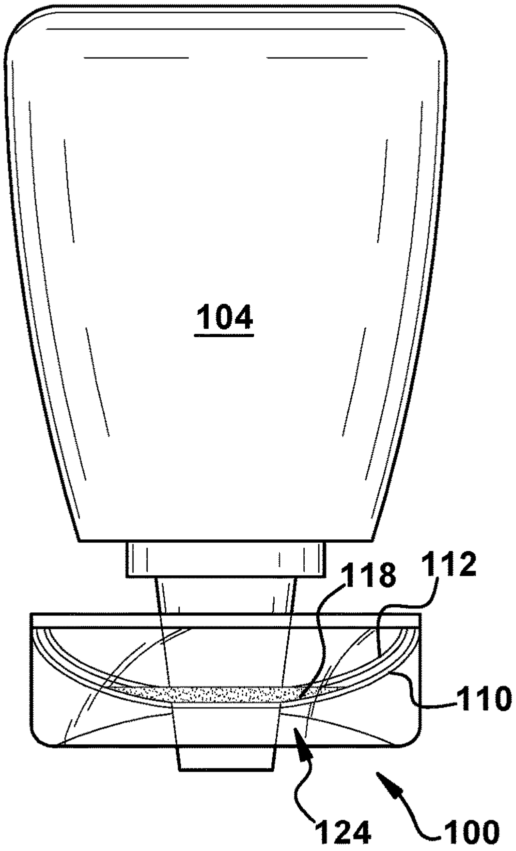
FIG. 16A is a schematic partial side view of the apparatus of FIG. 14 engaged with the eye dropper bottle in a first, vertical position.
Figure 17A:
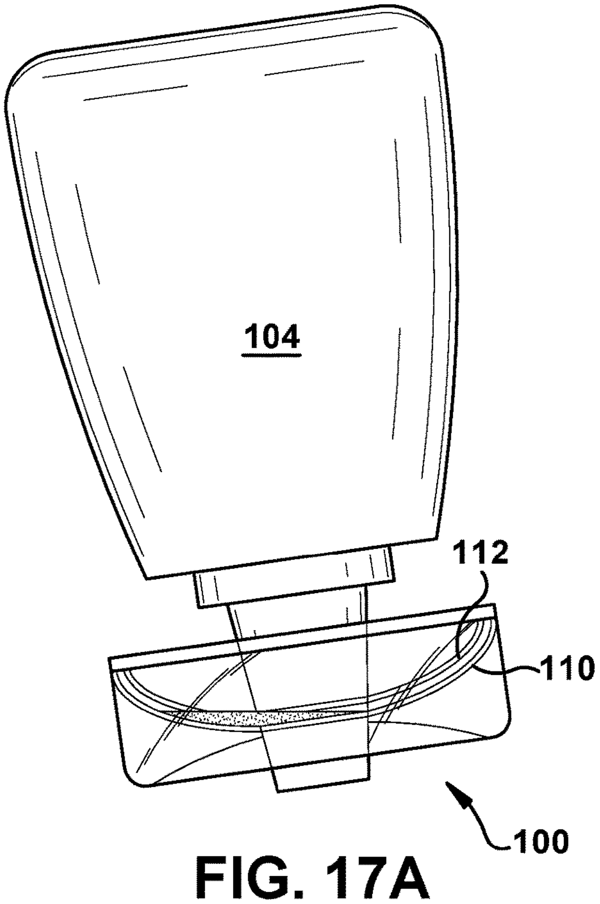
FIG. 17A is a schematic partial side view of the apparatus of FIG. 14 engaged with the eye dropper bottle in a second, non-vertical position.
Figure 16B:
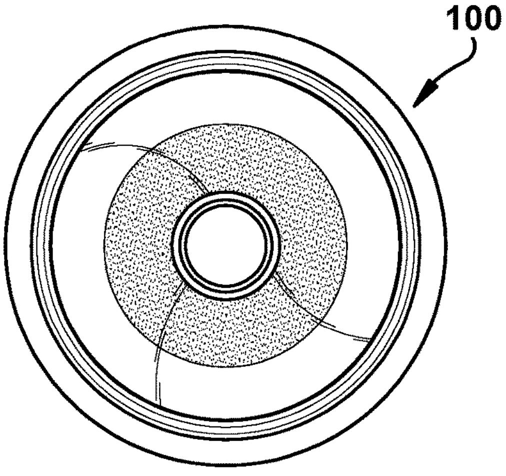
FIG. 16B is a schematic bottom view of the apparatus of FIG. 14 in the first, vertical position.
Figure 17B:
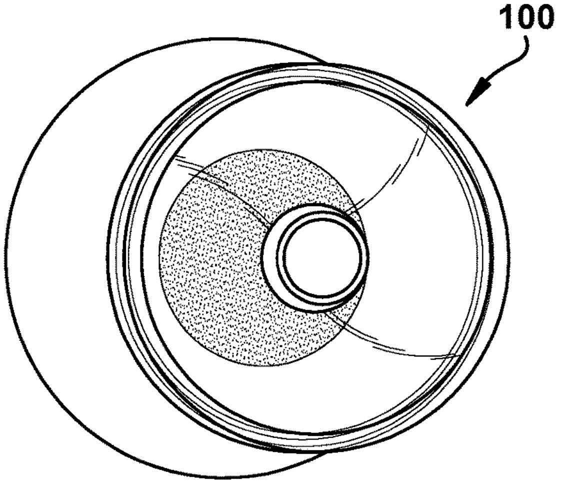
FIG. 17B is a schematic bottom view of the apparatus of FIG. 12 in the second, non-vertical position.

It should be noted that, while the tubular hub 106 is shown schematically in FIG. 14, a backing disc 130 could also or instead be provided to the apparatus 100. When present, the backing disc 130 could have a center aperture configured to accept a predetermined depth of the dropping nozzle 102 therethrough, and thus act, in concert with a center aperture of the auxiliary disc 128 and/or the first and second center apertures of the first and second discs 110, 112, in a "holdaway" fashion that obviates the need for a longitudinally extending tubular hub 106 structure. However, in order to form the indicator space 116, the first and second center apertures would need to be connected in a fluid tight manner, and either a direct seam therebetween or a "bridging" structure would be considered to serve a tubular hub 106 function.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An apparatus for assisting with alignment of a dropping nozzle of an eye dropper bottle, the apparatus comprising:

a tubular hub configured for selective engagement with the dropping nozzle to selectively laterally surround the dropping nozzle within a hub lumen thereof;

a first semispherical disc having a first center aperture and a first disc rim, spaced radially apart from the first center aperture by a first disc body, the first center aperture laterally surrounding an outer wall of the tubular hub, and the first disc body being semispherically curved between the first center aperture and the first disc rim;

a second semispherical disc having a second center aperture and a second disc rim, spaced radially apart from the second center aperture by a second disc body, the second center aperture laterally surrounding the outer wall of the tubular hub at a location thereupon longitudinally spaced from the first center aperture, and the second disc body being semispherically curved between the second center aperture and the second disc rim;

wherein the first and second disc rims are attached together at a rim perimeter to laterally enclose a substantially fluid tight toroidal indicator space longitudinally between the first and second disc bodies and radially between the outer wall of the tubular hub and the rim perimeter; and wherein at least one user-perceptible liquid is located within the indicator space, the liquid shifting with respect to the tubular hub under influence of gravity responsive to an angular position of the tubular hub, wherein the first disc body comprises an inner surface and a outer surface, the inner surface positioned closer to the second disc body than the outer surface, the inner surface at least partially defining a cavity, wherein the second semispherical disc is positioned entirely within the cavity in a manner that the second disc rim does not extend past the first disc rim.

2. The apparatus of claim 1, wherein the user-perceptible liquid is substantially symmetrically distributed within the indicator space, surrounding the tubular hub, when the tubular hub is substantially vertically located with respect to a ground surface.

3. The apparatus of claim 1, wherein a is located within the indicator space, and wherein the at least one user-perceptible liquid is urged toward the tubular hub responsive to the relative densities of the transparent liquid and the at least one user-perceptible liquid.

4. The apparatus of claim 3, wherein the transparent liquid is water and the at least one user-perceptible liquid is dyed mineral oil.

5. The apparatus of claim 1, wherein the tubular hub is a truncated cone with the hub lumen configured to accept a conical dropping nozzle.

6. The apparatus of claim 1, wherein at least one of the first and second discs is concave in a top-to-bottom direction of the apparatus, such that the corresponding disc rim is located below the corresponding disc center aperture.

7. The apparatus of claim 1, wherein at least one of the first and second discs is convex in a top-to-bottom direction of the apparatus, such that the corresponding disc rim is located above the corresponding disc center aperture.

8. The apparatus of claim 1, wherein at least one of the first and second discs includes a diffuser coating on at least a portion of the corresponding disc body, the diffuser coating being a different color from a color of the user-perceptible liquid.

9. The apparatus of claim 1, wherein at least one of the first and second discs includes a reflective coating on at least a portion of the corresponding disc body, the reflective coating facing longitudinally downward to selectively reflect a portion of a user's eye, when the tubular hub is engaged with the dropping nozzle.

10. The apparatus of claim 9, wherein the reflective coating is at least partially translucent and configured to allow viewing of the user-perceptible liquid therethrough.

11. The apparatus of claim 1, including a tip obstructor associated with the tubular hub, the tip obstructor selectively occluding at least a portion of an available cross-sectional flow area of the dropping nozzle to restrict an amount of fluid flow permitted to egress the eye dropper bottle.

12. A method of aligning a dropping nozzle of an eye dropper bottle with an eye of a patient, the method comprising:

providing an apparatus including a tubular hub, a first semispherical disc having a first center aperture and a first disc rim, spaced radially apart from the first center aperture by a first disc body, the first center aperture laterally surrounding an outer wall of the tubular hub, and the first disc body being semispherically curved between the first center aperture and the first disc rim, a second semispherical disc having a second center aperture and a second disc rim, spaced radially apart from the second center aperture by a second disc body, the second center aperture laterally surrounding the outer wall of the tubular hub at a location thereupon longitudinally spaced from the first center aperture, and the second disc body being semispherically curved between the second center aperture and the second disc rim, the first and second disc rims being attached together at a rim perimeter to laterally enclose a substantially fluid tight toroidal indicator space longitudinally between the first and second disc bodies and radially between the outer wall of the tubular hub and the rim perimeter, and at least one user-perceptible liquid located within the indicator space;

shifting a position of the user-perceptible liquid within the indicator space with respect to the tubular hub under influence of gravity responsive to an angular position of the tubular hub;

engaging the dropping nozzle with the tubular hub to selectively laterally surround the dropping nozzle within a hub lumen; and substantially symmetrically distributing the liquid within the indicator space, surrounding the tubular hub, to indicate that the dropping nozzle is substantially vertically located with respect to a ground surface, wherein the first disc body comprises an inner surface and an outer surface, the inner surface positioned closer to the second disc body than the outer surface, the inner surface at least partially defining a cavity, wherein the second semispherical disc is positioned entirely within the cavity in a manner that the second disc rim does not extend past the first disc rim.

13. The method of claim 12, including coating at least a portion of a corresponding disc body of at least one of the first and second discs with a diffuser coating on at least a portion of the corresponding disc body, the diffuser coating being a different color from a color of the user-perceptible liquid, wherein the method includes providing, with the diffuser coating, a user-perceptible contrast between the user-perceptible liquid and a portion of the indicator space which lacks user-perceptible liquid.

14. The method of claim 12, including coating at least a portion of a corresponding disc body of at least one of the first and second discs with a reflective coating on at least a portion of the corresponding disc body, the method including selectively reflecting, with the reflective coating, an image of at least a portion of a user's eye.

15. The method of claim 14, wherein the reflective coating is at least partially translucent, and wherein the method includes allowing a user to view the user-perceptible liquid through the reflective coating, concurrently with the reflective coating reflecting the image of at least the portion of the user's eye.

16. The method of claim 15, including the step of indicating to the user, via concurrent viewing of the user-perceptible liquid and the image of at least the portion of the user's eye, that a predetermined alignment position of the dropping nozzle with the user's eye has been achieved.

17. An apparatus for assisting with alignment of a dropping nozzle of an eye dropper bottle, the apparatus comprising:

a tubular hub configured for selective engagement with the dropping nozzle to directly attach to the dropping nozzle within a hub lumen thereof; and a container directly attached to an outer wall of the tubular hub, the container comprising:

a first semispherical disc having a first center aperture and a first disc rim, spaced radially apart from the first center aperture by a first disc body, the first center aperture laterally surrounding the outer wall of the tubular hub, and the first disc body being semispherically curved between the first center aperture and the first disc rim;

a second semispherical disc having a second center aperture and a second disc rim, spaced radially apart from the second center aperture by a second disc body, the second center aperture laterally surrounding the outer wall of the tubular hub at a location thereupon longitudinally spaced from the first center aperture, and the second disc body being semispherically curved between the second center aperture and the second disc rim;

wherein the first and second disc rims are attached together at a rim perimeter to laterally enclose a substantially fluid tight toroidal indicator space longitudinally between the first and second disc bodies and radially between the outer wall of the tubular hub and the rim perimeter; and wherein at least one user-perceptible liquid is located within the indicator space, the at least one user-perceptible liquid shifting with respect to the tubular hub under influence of gravity responsive to an angular position of the tubular hub wherein the first disc body comprises an inner surface and an outer surface, the inner surface positioned closer to the second disc body than the outer surface, the inner surface at least partially defining a cavity, wherein the second semispherical disc is positioned entirely within the cavity in a manner that the second disc rim does not extend past the first disc rim.

18. The apparatus of claim 17, wherein the indicator space comprises a C-shaped cross section.

* * * * *